United States Patent [19]

Elam et al.

[11] Patent Number: 4,551,523

[45] Date of Patent: Nov. 5, 1985

[54] PREPARATION OF SACCHARIDE ACETOACETATES

[75] Inventors: Edward U. Elam; Michael L. Middleton, both of Kingsport, Tenn.

[73] Assignee: Eastman Kodak Company, Rochester, N.Y.

[21] Appl. No.: 484,807

[22] Filed: Apr. 14, 1983

[51] Int. Cl.$^4$ ................................................ C07H 1/00
[52] U.S. Cl. .................................... 536/119; 536/18.2; 536/115; 536/18.6
[58] Field of Search ...................... 536/115, 119, 18.2, 536/18.6

[56] References Cited

U.S. PATENT DOCUMENTS 2,174,541  10/1939  Walthausen et al. ............... 536/119
2,628,249  2/1953  Bruno et al. ........................ 236/119

OTHER PUBLICATIONS

Carroll et al., "Journ. Amer. Chem. Soc.", vol. 75, pp. 5400–5402, 1953.

*Primary Examiner*—Johnnie R. Brown
*Attorney, Agent, or Firm*—J. Frederick Thomsen; D. B. Reece, III

[57] ABSTRACT

Disclosed is a process for the preparation of mono- and di-saccharide acetoacetates by the reaction of a mono- or di-saccharide with 2,2,6-trimethyl-4H-1,3-dioxin-4-one.

5 Claims, No Drawings

PREPARATION OF SACCHARIDE ACETOACETATES

DESCRIPTION

This invention pertains to a novel process for the preparation of mono- and di-saccharide acetoacetates.

Esters of acetoacetic (2-oxobutanoic) acid most commonly are prepared by the reaction of diketene with alcohols and by transesterification using an alkyl acetoacetate. The preparation of sucrose acetoacetates by the reaction of diketene and sucrose in dimethylformamide in the presence of triethylamine catalyst has been disclosed by Dalton, J. Appl. Chem., 13(7), 277 (1963). When we employed this method to prepare sucrose acetoacetates and other saccharide acetoacetates black, syrupy products were obtained. The procedure described by Dalton also is commercially unattractive since the dimethylformamide solvent can be removed from the crude product only by distillation under very high vacuum.

Acetoacetate esters also have been prepared from alcohols and 2,2,6-trimethyl-4H-1,3-dioxin-4-one (2,2,4-trimethyl-6-keto-1,3-dioxene, TKD) prepared by the reaction of diketene and acetone. For example, the preparation of butyl acetoacetate by the reaction of butanol and TKD in the presence of p-toluenesulfonic acid catalyst has been reported by Carroll et al, J. Am. Chem. Soc., 75, 5402 (1953). Application of the method of Carroll et al to glucose gave only trace amounts of unknown products.

We have discovered that mono- and di-saccharide acetoacetates of improved purity can be obtained by reacting a mono- or di-saccharide with TKD while removing acetone from the reaction mixture. Our process requires neither a catalyst nor a solvent which simplifies product isolation and purification.

Examples of the mono-saccharides which may be used in our novel process include glucose, mannose, galactose, fructose and sorbose. Maltose, lactose and sucrose are typical of the di-saccharides useful in the process. The products obtained in accordance with our invention are mixtures of saccharides which have been acetoacetylated to varying degrees with the predominant ester being determined by the mole ratio of saccharide:TKD employed. Thus, the saccharide:TKD mole ratio is not critical and depends upon the degree of esterification desired. Excess TKD, if used, will either remain unchanged or be converted to dehydroacetic acid and acetone, depending upon the reaction conditions.

Reaction of the mono- or di-saccharide generally occurs at a reasonable rate at temperatures in the range of about 80° to 130° C. The use of lower temperatures, while usually operable to some degree, gives slow reaction rates whereas the use of higher temperatures offers no advantages and may result in degradation of the reactants and/or products. Although not required by our process, an inert, organic solvent, preferably one that permits the use of a reaction temperature greater than 80° C., may be used if desired. Hydrocarbons such as toluene, xylene and heptane, esters such as propyl and butyl acetate and ketones such as diethyl or methyl isobutyl ketone are examples of suitable solvents.

Under optimum conditions the process produces only acetone and acetoacetylated mono- and/or di-saccharides. The acetone is stripped under vacuum and the residue, which usually is an amber, noncrystalline syrup, may be used as such or purified by such techniques as molecular distillation or column chromatography.

The saccharide acetoacetates provided by our invention may be reacted with formaldehyde, as described by Dalton for the sucrose compounds, to give resins which may be cast from suitable solvents to give hard, glossy films. The products also are useful as chelating agents for solubilizing metallic compounds in organic solvents and potentially as high caloric source compounds for human pharmaceutical use.

The process of our invention is further illustrated by the following examples.

EXAMPLE 1

Into a nitrogen-purged 300 ml, 3-neck flask equipped with a mechanical stirrer, thermocouple, and a Dean-Stark trap is placed 90 g. (0.5 mol) α-D-glucose and 355 g. (2.5 mol) TKD. The mixture is stirred and heated to 100°–110° C. and 132 g. acetone is distilled off over a 1½ hour period. The mixture is heated to and held at 120° C. for 30 minutes and then allowed to cool. Residual acetone is removed under reduced pressure at 45° C. The product is a clear, viscous syrup. Mass spectrometry indicates that the major component of the crude product (285 g.) is α-D-glucose pentaacetoacetate along with partially acetoacetylated α-D-glucose compounds. The 1H nmr spectrum (CDCl$_3$) contained resonances at 3.60 ppm characteristic of the

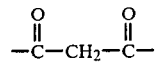

group, and at 2.30 ppm characteristic of the

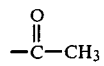

group.

Anal. Calculated for C$_{26}$H$_{32}$O$_{16}$: C;52.04%, H;5.37%. Found: C;52.11%, H;5.45%.

EXAMPLE 2

According to the procedure described in Example 1 a mixture of 36 g. (0.2 mol) α-D-glucose and 85.2 g. (0.6 mol) TKD is heated at 100°–110° C. for 1 hour during which 34 g. acetone is collected. The temperature of the mixture is increased to and held at 135° C. for 20 minutes, the heat source is removed and the reaction mixture is allowed to cool with residual acetone being removed under reduced pressure to leave a clear, very viscous syrup. Mass spectrometry of the crude product indicates it consists primarily of α-D-glucose triacetoacetate and minor amounts of mono- and diacetoacylated glucose. The 1H nmr spectrum (CDCl$_3$) contained resonances as described in Example 1. Anal. Calculated for C$_{18}$H$_{25}$O$_{12}$: C;50.00%, H;5.59%. Found C;50.37%, H;5.75%.

EXAMPLE 3

According to the procedure described in Example 1 34.1 g. (0.1 mol) of finely ground sucrose is reacted with 113.6 (0.8 mol) at 95°–105° C. for 2½ hours while 36 g. of acetone is distilled off. The product is decanted from 9.5 g. unreacted sucrose and the residual acetone is removed. The crude syrupy product weighs 100 g.

EXAMPLE 4

According to the procedure described in Example 1 34.2 g. of maltose hydrate is reacted with 134 g. TKD at 100°–115° C. for 1 hour during which time 56 g. acetone is collected. The reaction mixture is further heated at 130° C. for 30 minutes and then allowed to cool with residual acetone being removed under reduced pressure. The crude syrupy product weighs 93 g.

EXAMPLE 5

According to the procedure described in Example 1 36 g. (0.2 mol) fructose is reacted with 142 g. (1 mol) TKD at 100°–110° C. while 50 g. acetone is collected over a 2-hour period. The reaction mixture is allowed to cool and residual acetone is removed to give 102 g. crude syrupy product.

EXAMPLE 6

A mixture of 4.8 g. of glucose pentaacetoacetate, prepared as described in Example 1, 2.5 g. of an approximately 50% solution of formaldehyde in methanol ("Methyl Formcel") are dissolved in 10 ml of methanol, a drop of morpholine is added, and the solution is used to coat steel panels. After standing for a few hours, or heating briefly to 60° C., the material has formed a hard, clear coating which adheres strongly to the metal and is not affected by water. Similar clear, strongly adherent coatings may be formed on glass and wood.

Coatings with similar characteristics can be made using different ratios of formaldehyde to glucose pentaacetoacetate. The amount of catalyst used is not critical although the curing time will be decreased as larger amounts are used. Other weak organic bases such as piperidine, triethylamine, and the like may also be used as catalysts. If no catalyst is used, the curing time of the film is greatly increased and the ultimate hardness is lower.

Similar coatings may be made from the acetoacetates of the other mono- and di-saccharides described hereinabove. The coating made as described above from glucose pentaacetoacetate differs from one made similarly from sucrose acetoacetate in that the glucose-derived coating is much less colored and more resistant to the action of water.

The invention has been described in detail with particular reference to preferred embodiments thereof, but it will be understood that variations and modifications can be effected within the spirit and scope of the invention.

We claim:

1. A process for the preparation of mono- and di-saccharide acetoacetates which comprises reacting a mono- or di-saccharide with 2,2,6-trimethyl-4H-1,3-dioxin-4-one.

2. A process according to claim 1 wherein glucose is reacted with 2,2,6-trimethyl-4H-1,3-dioxin-4-one at a temperature of about 80° to 130° C.

3. A process according to claim 1 wherein maltose is reacted with 2,2,6-trimethyl-4H-1,3-dioxin-4-one at a temperature of about 80° to 130° C.

4. A process according to claim 1 wherein sucrose is reacted with 2,2,6-trimethyl-4H-1,3-dioxin-4-one at a temperature of about 80° to 130° C.

5. A process according to claim 1 wherein fructose is reacted with 2,2,6-trimethyl-4H-1,3-dioxin-4-one at a temperature of about 80° to 130° C.

* * * * *

UNITED STATES PATENT AND TRADEMARK OFFICE
CERTIFICATE OF CORRECTION

PATENT NO. : 4,551,523

DATED : November 5, 1985

INVENTOR(S) : Edward U. Elam and Michael L. Middleton

It is certified that error appears in the above-identified patent and that said Letters Patent is hereby corrected as shown below:

Column 4, line 21, after "dioxin-4-one" the following should be inserted:

--- in the absence of added catalyst and solvent; removing acetone formed during the reaction and recovering the mono- and di-saccharide acetoacetates. ---

Signed and Sealed this

Twenty-eighth Day of January 1986

[SEAL]

Attest:

DONALD J. QUIGG

Attesting Officer

Commissioner of Patents and Trademarks